(12) United States Patent
Belafsky et al.

(10) Patent No.: US 7,882,840 B2
(45) Date of Patent: Feb. 8, 2011

(54) PASSAGE EXPANSION DEVICE FOR PATIENTS

(75) Inventors: Peter Belafsky, Davis, CA (US); Joel Delman, Chicago, IL (US); John B. Freese, Evanston, IL (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/910,331

(22) PCT Filed: Apr. 4, 2006

(86) PCT No.: PCT/US2006/012726

§ 371 (c)(1),
(2), (4) Date: Nov. 13, 2008

(87) PCT Pub. No.: WO2006/108066

PCT Pub. Date: Oct. 12, 2006

(65) Prior Publication Data

US 2009/0137859 A1    May 28, 2009

Related U.S. Application Data

(60) Provisional application No. 60/668,530, filed on Apr. 4, 2005.

(51) Int. Cl.
*A61B 19/00* (2006.01)
(52) U.S. Cl. .................................................. 128/898
(58) Field of Classification Search ............... 600/9–15; 128/897, 899; 606/138–158
See application file for complete search history.

(56) References Cited

U.S. PATENT DOCUMENTS

| 3,926,175 | A | 12/1975 | Allen et al. |
| 4,474,181 | A * | 10/1984 | Schenck ...................... 606/155 |
| 4,511,330 | A * | 4/1985 | Smiley et al. ................. 433/18 |
| 5,176,618 | A | 1/1993 | Freedman |
| 5,817,000 | A | 10/1998 | Souder |
| 5,823,938 | A | 10/1998 | Hernandez |
| 6,013,071 | A | 1/2000 | Moisdon et al. |
| 6,234,956 | B1 | 5/2001 | He |
| 7,360,542 | B2 * | 4/2008 | Nelson et al. ............... 128/848 |
| 7,445,010 | B2 * | 11/2008 | Kugler et al. ............... 128/897 |
| 2004/0034396 | A1 * | 2/2004 | Freed et al. .................... 607/72 |
| 2004/0049102 | A1 | 3/2004 | Nelson et al. |
| 2004/0134491 | A1 | 7/2004 | Pflueger et al. |
| 2004/0153127 | A1 * | 8/2004 | Gordon et al. ................ 607/1 |
| 2004/0181116 | A1 * | 9/2004 | Kent et al. ..................... 600/9 |

FOREIGN PATENT DOCUMENTS

WO    WO 2004/084709 A1    10/2004

* cited by examiner

*Primary Examiner*—Charles A Marmor, II
*Assistant Examiner*—Christine D Hopkins
(74) *Attorney, Agent, or Firm*—Townsend and Townsend and Crew LLP

(57) ABSTRACT

A method for opening a portion of a passageway of a patient is disclosed. The patient has a first metallic structure attached to a portion of the patient's neck. The method includes obtaining a second magnetic structure, placing the second magnetic structure proximate the first metallic structure attached to the portion of the patient's neck, and pulling the second magnetic structure away from the patient's neck to thereby open the passageway.

2 Claims, 9 Drawing Sheets

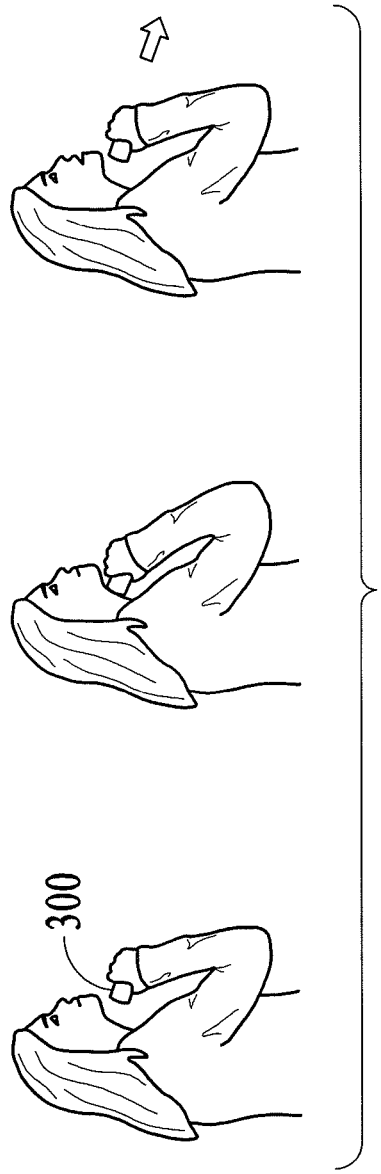
FIG.6
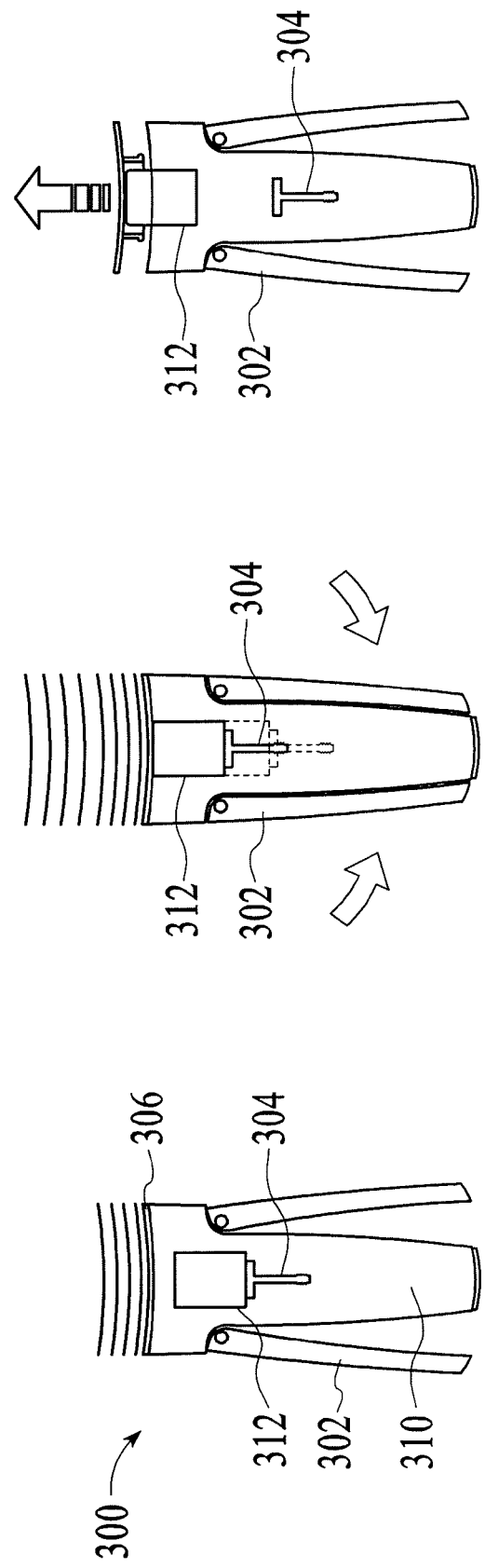
FIG.7A
FIG.7B
FIG.7C

PASSAGE EXPANSION DEVICE FOR PATIENTS

CROSS-REFERENCES TO RELATED APPLICATIONS

This application is a National Stage of International Patent Application No. PCT/US2006/012726, filed Apr. 4, 2006, and claims the benefit of U.S. Provisional Application 60/668,530, filed on Apr. 4, 2005, which are herein incorporated by reference in their entirety for all purposes.

STATEMENT AS TO RIGHTS TO INVENTIONS MADE UNDER FEDERALLY SPONSORED RESEARCH AND DEVELOPMENT

Not applicable

BACKGROUND OF THE INVENTION

Up to 50 percent of individuals over the age of 60 suffer from dysphagia. In the year 2000, there were more than 270,000 patients diagnosed with dysphagia in the Veteran's Affairs (VA) Hospitals alone. Although tens of millions of individuals in the United States suffer from dysphagia, there are few treatments. Treatment options include swallowing therapy, diet restriction, non-oral feeding, and a few invasive surgical options with questionable benefit.

It would be desirable if there were better ways to treat conditions such as dysphagia.

SUMMARY OF THE INVENTION

Embodiments of the invention are directed to methods, systems, and devices that can be used to treat conditions such as dysphagia.

One embodiment of the invention is directed to a method for opening a portion of a passageway of a patient, such as the upper esophageal sphincter or UES, where the patient has a first metallic structure attached to a portion of a patient's neck. The method includes obtaining a second magnetic structure, and placing the second magnetic structure proximate the first metallic structure attached to the portion of the patient's neck. The patient then pulls the second magnetic structure away from the patient's neck to thereby open the passageway (or upper valve or sphincter of the esophagus (UES)).

Another embodiment of the invention is directed to a magnetic device, for use with a first metallic structure implanted in a portion of a patient's neck. The magnetic device includes a handle, and a second magnetic structure, where the second magnetic structure is adapted to attract to the first metallic structure across the skin, and thereby open the upper esophageal sphincter of a patient.

Another embodiment of the invention is directed to a method for opening a passageway in a patient. The method includes placing a structure such as a suture, implant, or a magnetic structure in the patient proximate the passageway, and pulling the structure away from the patient to open the passageway.

Other embodiments of the invention are directed to systems that include the above-described first and second magnetic structures.

These and other embodiments of the invention are described in further detail below.

BRIEF DESCRIPTION OF THE DRAWINGS

FIG. 6 shows various images of a person using a magnetic device according to an embodiment of the invention.

FIGS. 7(a)-7(c) show schematic side views of a magnetic device, wherein the second magnetic structure in the magnetic device is in different positions.

In the Figures, like numerals designate like elements.

DETAILED DESCRIPTION

To address the above problems, a device such as a magnet, suture, or the like may be placed adjacent to a passageway (e.g., the upper esophageal sphincter) in a patient. The device can be pulled by the patient away from the patient to open the swallowing passageway. Embodiments of the invention would give people back the precious gift of swallowing.

Preferred embodiments of the invention use magnetic structures to open a patient's passageway. As used herein, the term "magnetic material" includes materials that are capable of being magnetized or capable of being attracted to a magnet. The magnetic structures can attract each other across the skin and would serve to pull the cricopharyngeous (upper valve of the esophagus) open, thereby allowing persons with oropharyngeal dysphagia to swallow. In embodiments of the invention, a first metallic, or first magnetic structure (which may be, for example, paramagnetic or ferromagnetic) can be placed under the skin through a minimally invasive procedure that can be performed under local anesthesia. Once the skin heals, an external second magnetic structure (which may also be, for example, paramagnetic or ferromagnetic) can attract the implanted first magnetic structure across the cervical skin. Traction on the second, external magnetic structure pulls the upper valve of the esophagus open and allows food to pass. In some cases, the second magnetic structure may be referred to as a "swallow magnet" or "swallow device".

Placing magnets and other metals in the body has precedent in medicine. Head and neck surgeons place metal plates in the body to repair facial fractures on a daily basis. Cochlear implants utilize magnets to affix transmitters to receivers across the skin. Magnets have been placed in the eyelid to close the eye of persons with facial paralysis. The inventive swallow expansion device provides for a novel treatment for swallowing disorders. Given the millions of individuals with oropharyngeal dysphagia, the potential of this invention is limitless. Embodiments of the invention are inexpensive to develop, and are technically easy to place under the skin. If any problems develop, the implanted magnetic structure can be easily removed or replaced.

Figure 1:
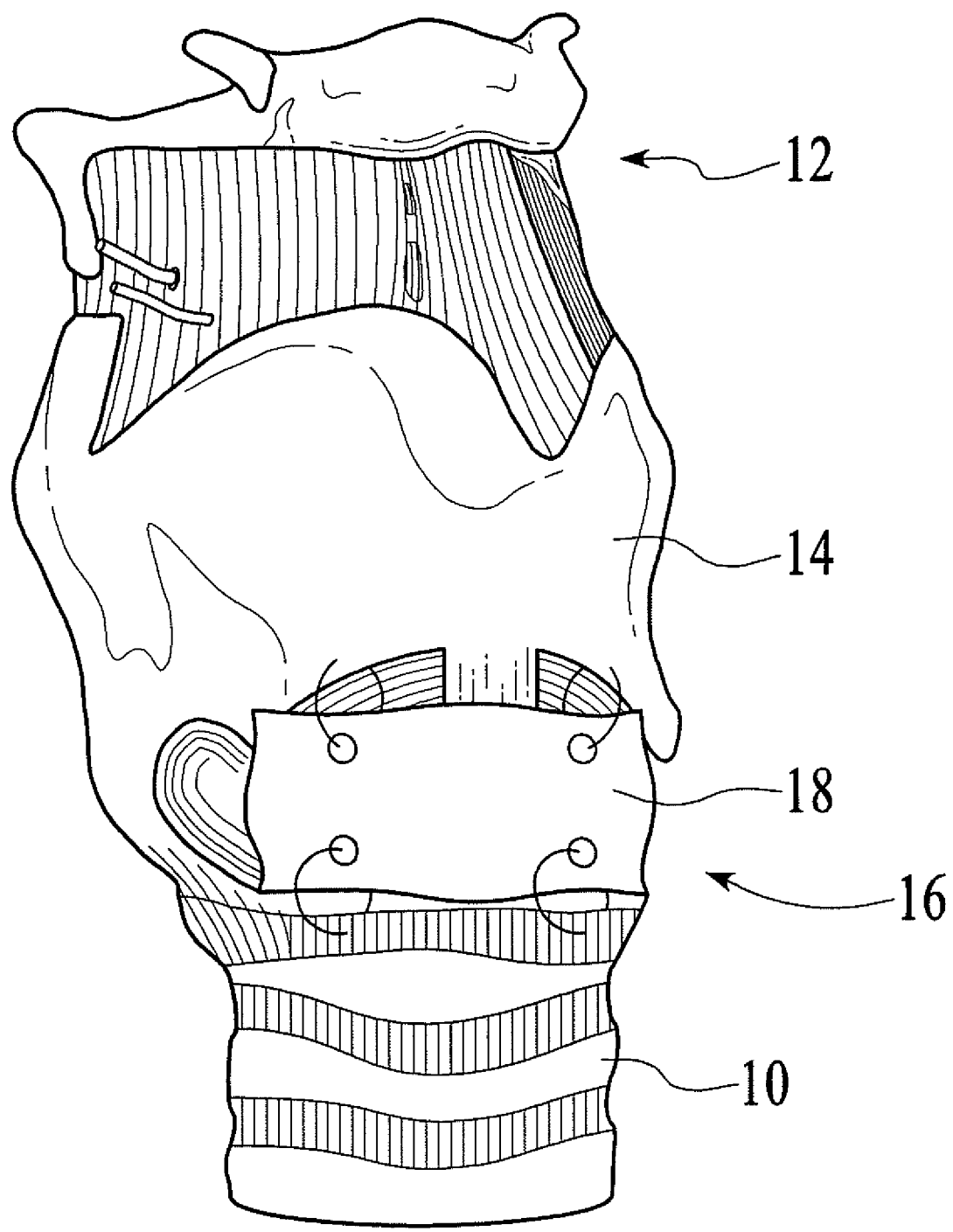
FIG. 1 shows a diagram of portions of a patient's throat with a first magnetic (or metallic) structure attached to the cricoid and thyroid cartilages.

FIG. 1 shows some portions of a patient's neck including a hyoid bone 12, thyroid cartilage 14, cricoid cartilage 16, and the trachea 10. In embodiments of the invention, an internal first magnetic structure 16 is secured to the cricoid and thyroid cartilages through a small skin incision. This can be done with local anesthesia and would only be considered a minimally invasive procedure. The skin would then be closed over the first magnetic structure and would then be allowed to heal.

The internal first magnetic structure 16 may be in any form and may include any suitable material. As noted below, it may be part of a more complex implant assembly. It may have a rectangular or circular shape, and may include any suitable magnetic material (e.g., Fe, Fe—Co, Ni, electrical steel, etc.). The first magnetic structure 16 may alternatively or additionally include a number of holes or attachment points for sutures (or some other attachment mechanism) so that the internal magnet can be secured to cricoid and thyroid cartilages. The first magnetic structure 16 may also be coated with a biocompatible material such as titanium so that it may be rendered implantable.

Figure 2:
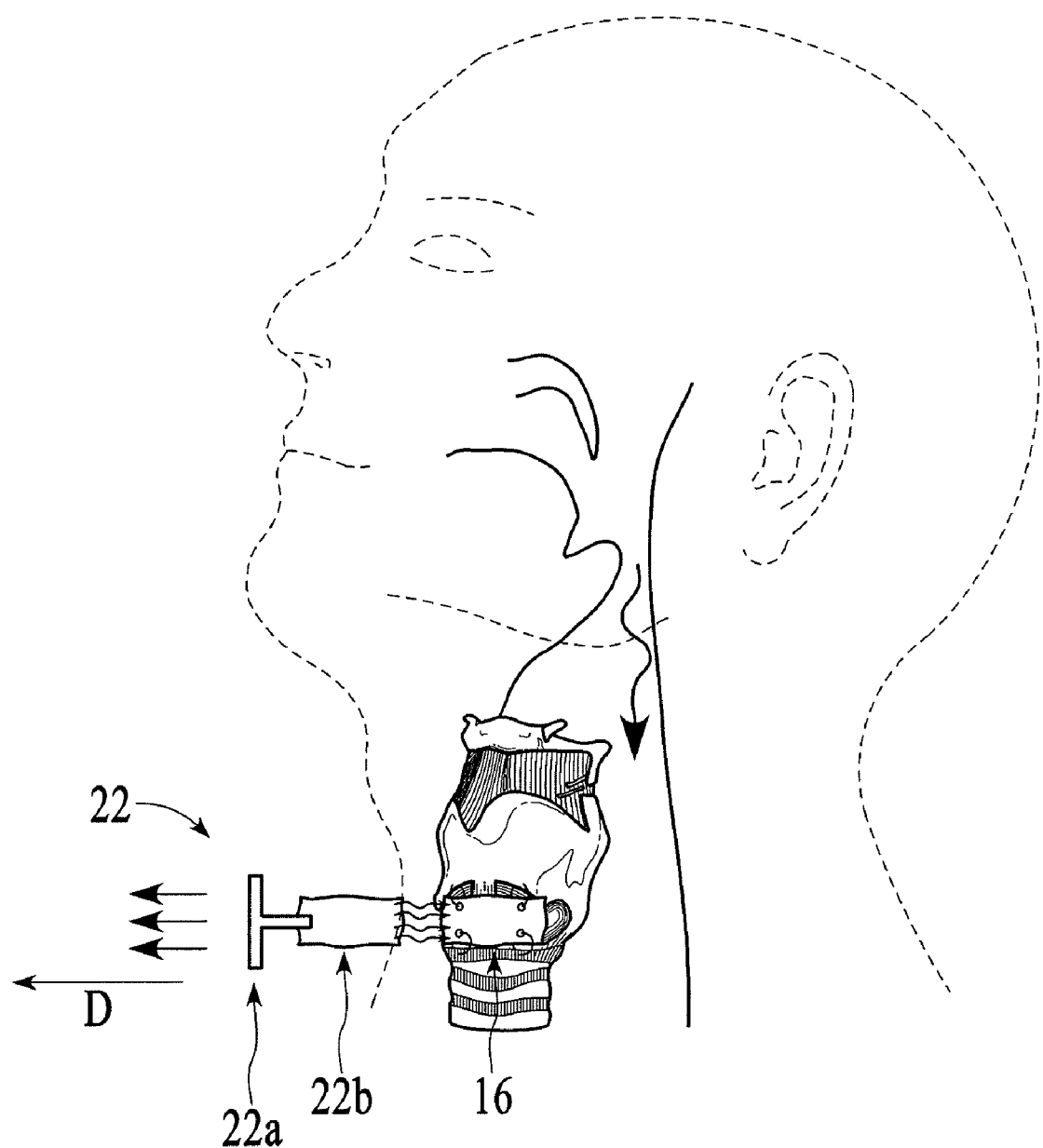
FIG. 2 shows a system including a first magnetic (or metallic) structure and second magnetic structure, as it would be used by a patient.

As shown in FIG. 2, a second magnetic structure 22(b) can be attached to a handle 22(a) in the form of a T-bar. The handle 22(a) and the second magnetic structure 22(b) may form a magnetic device 22. The second magnetic structure 22(b) is external to the patient, and would be used to attract the first magnetic structure 16 through the skin during meals. The first magnetic structure 16 is under the skin. Gentle anterior traction on the magnetic structures is achieved by pulling on the handle 22(b) in the direction D, thereby opening the upper sphincter (cricopharyngeal muscle) of the esophagus, allowing food to pass and allowing the patient to eat. The second magnetic structure 22(b) can be removed after the meal.

Like the first magnetic structure 16, the second magnetic structure 22(b) may be in any suitable form and may comprise any suitable magnetic material.

Figure 3A:
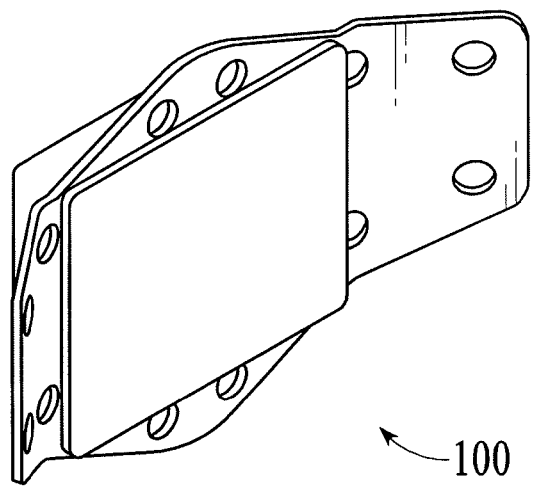
FIG. 3(a) shows a perspective, exploded view of an implant assembly according to an embodiment of the invention.
Figure 3B:
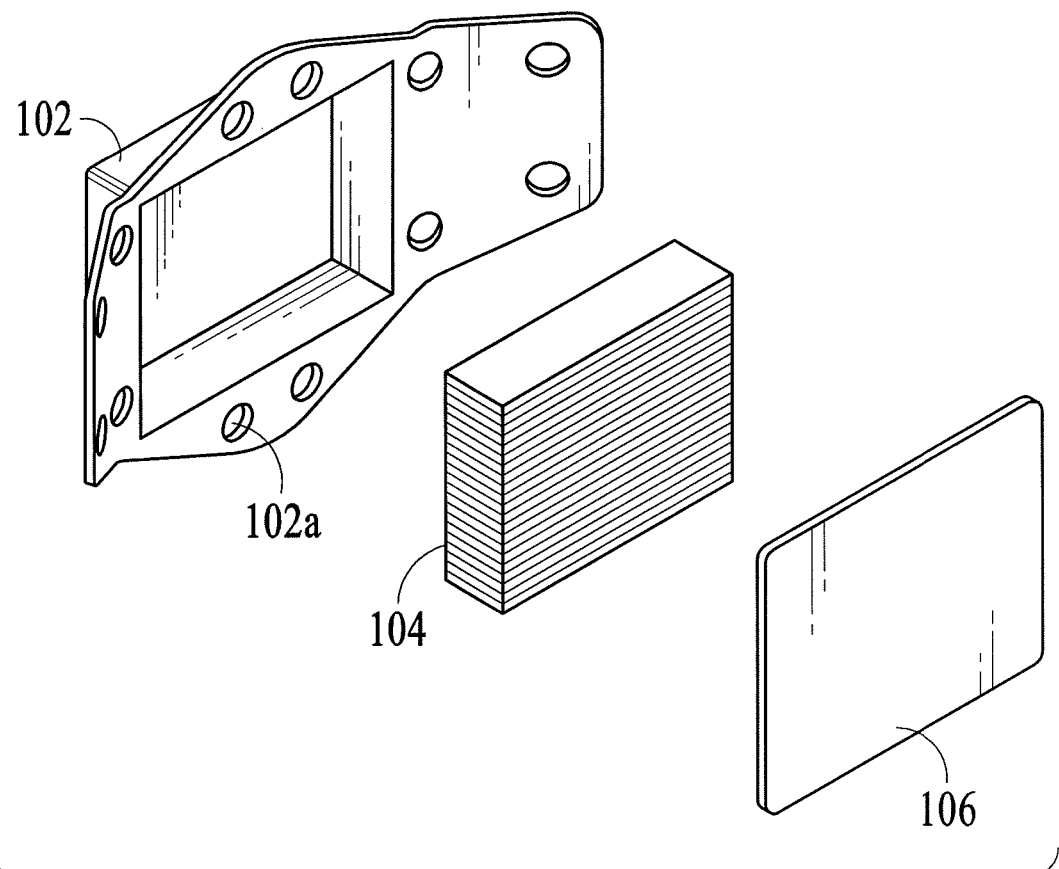
FIG. 3(b) shows a perspective view of the implant assembly shown in FIG. 3(a), in an assembled state.

FIG. 3(a) shows a perspective view of an implant assembly 100 according to an embodiment of the invention. As shown in FIG. 3(b), the implant assembly 100 includes a second magnetic structure 104, which is sandwiched between a titanium cup-shaped structure 102 and a titanium plate 106. The titanium cup shaped structure may include a number of holes 102(a) around a flange portion of the cup shaped structure 102. Sutures or other connecting structures may be used to secure the implant assembly 100 to a patient's cricoid. The titanium plate 106 may be welded or otherwise attached to the cup-shaped structure 102 to enclose the second magnetic structure 104.

Figure 4:
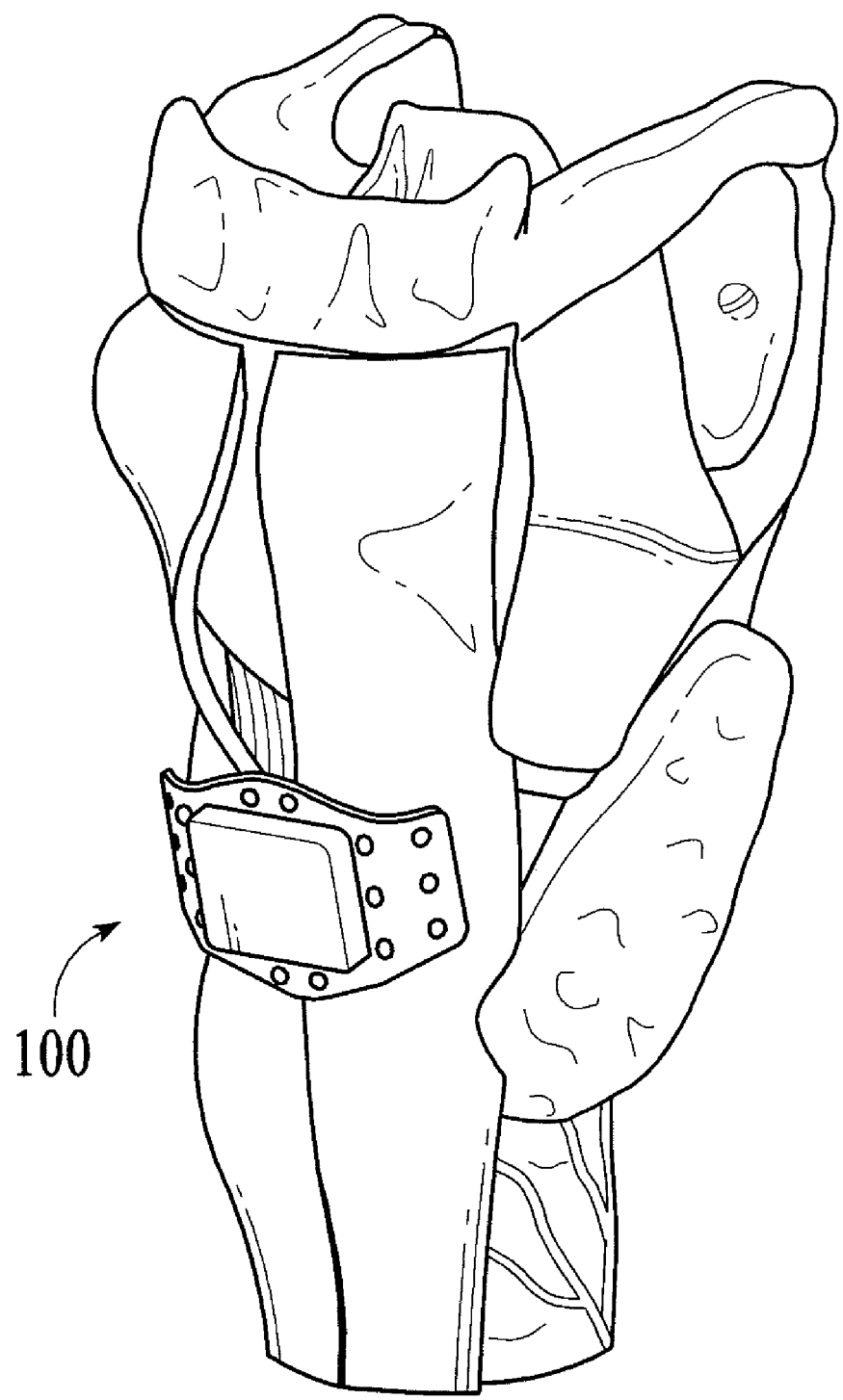
FIG. 4 shows a perspective view of the implant assembly shown in FIG. 3(b) as it would be attached to the cricoid and thyroid cartilages in a patient.

FIG. 4 shows how the implant assembly 100 that is shown in FIGS. 3(a) and 3(b) would be attached to a patient's cricoid.

Figure 5:
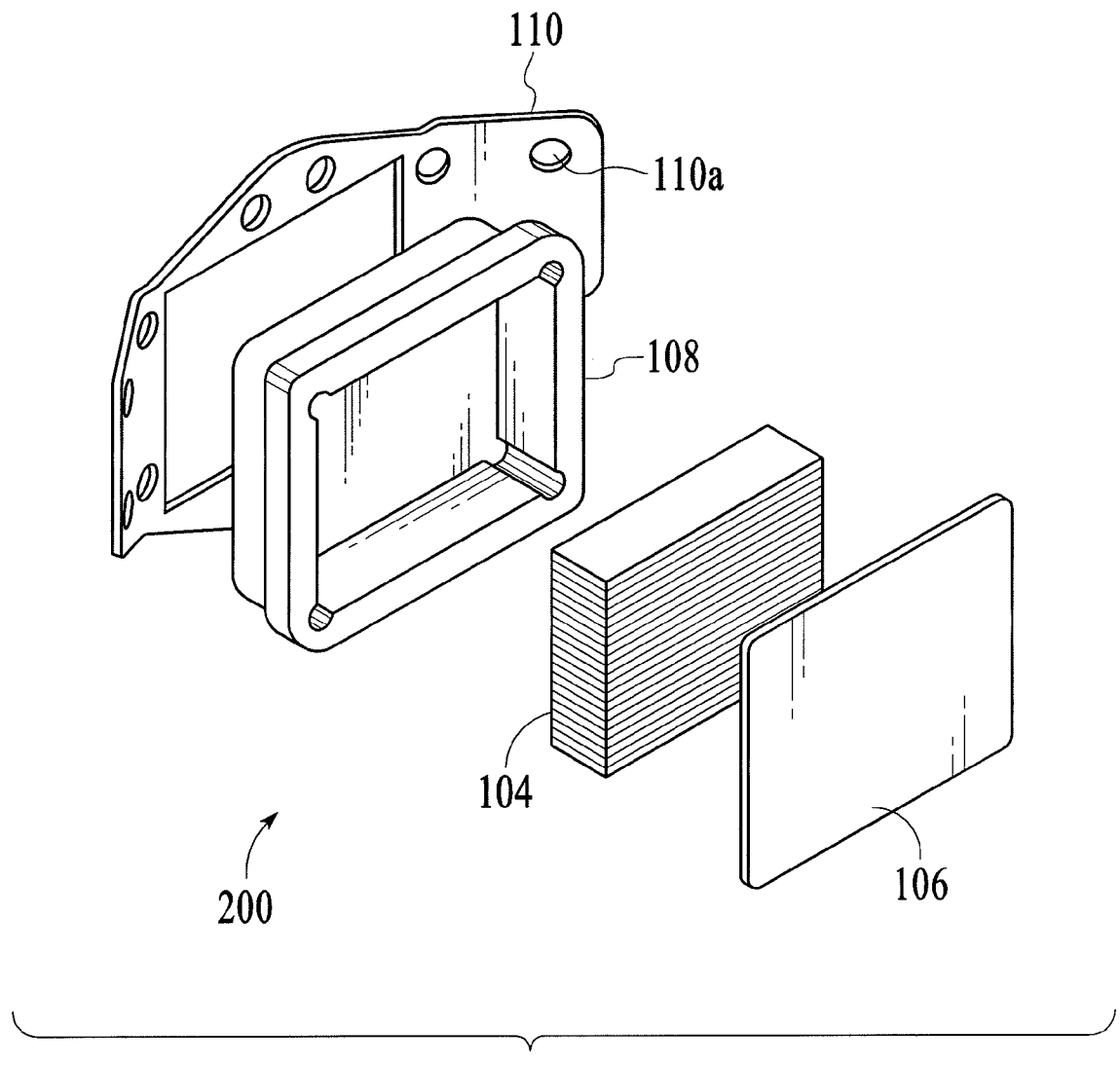
FIG. 5 shows a perspective view of another implant assembly embodiment. In this example, the implant assembly has a separate flange structure and a separate cup-shaped structure.

FIG. 5 shows another implant assembly 200 embodiment. In this embodiment, a flange structure 110 including holes 110(a) has a central aperture that receives a cup shaped structure 108 that has a peripheral flange. As in the implant assembly embodiment shown in FIG. 3(a) and FIG. 3(b), in the implant assembly 200 shown in FIG. 5, the second magnetic structure 104 is sandwiched between the cup shaped structure 108 and a titanium plate 106. The flange structure 110, the cup shaped structure 108, and the titanium plate 106 may be welded together.

Although titanium plates, cup-shaped structures, and flange structures are discussed in these examples, it is understood that the implant assemblies according to embodiments may include any number of additional components and may include any suitable type of biocompatible material.

FIG. 6 shows how a magnetic device according to an embodiment of the invention would be used. As shown in FIG. 6, a patient obtains and then places a magnetic device 300 including a second magnetic structure close to her neck and then pulls the magnetic device 300 away from her neck. The second magnetic structure (not shown) in the magnetic device 300 pulls the first magnetic device (not shown) implanted in the patient's neck. This pulls on the patient's cricopharyngeous muscle and opens the cervical esophagus, thereby allowing the patient to swallow.

FIG. 7(a) shows a magnetic device 300 including first and second handles 302, which are pivotably attached to a housing 310. A curved pad 306 is at the front portion of the device 300 and is intended to conform to the outer surface of a patient's neck. A pushing element 304 is attached to a second magnetic structure 312, and both of these components are in the housing 310. The second magnetic structure 312 is recessed in the housing 310 until the patient squeezes the handles 302. Minimal magnetic attraction between the interacting first and second magnetic structures allows comfortable placement and removal of the magnetic device 300.

FIG. 7(b) shows the magnetic device 300 when the user squeezes the handles 302. After squeezing the handles 302, the second magnetic structure 104 moves toward the front of the magnetic device 300 and magnetically engages a first magnetic structure that is implanted in the patient.

FIG. 7(c) shows the magnetic device 300 after the patient releases the handles 302. To avoid any damage to the cricoid, the magnetic device 300 may include an automatic release mechanism, which releases the second magnetic structure in the magnetic device 300 if the pulling force exceeds safe parameters (e.g., 7-10 lbs. of force).

The magnetic device 300 includes handles that control how much magnetic attraction is available to pull an internal implant forward in order to open the upper esophageal sphincter. Thin patients need less magnetic power than persons with thicker necks. The device can be adjusted to provide variable amounts of magnetic attraction.

Figure 8A:
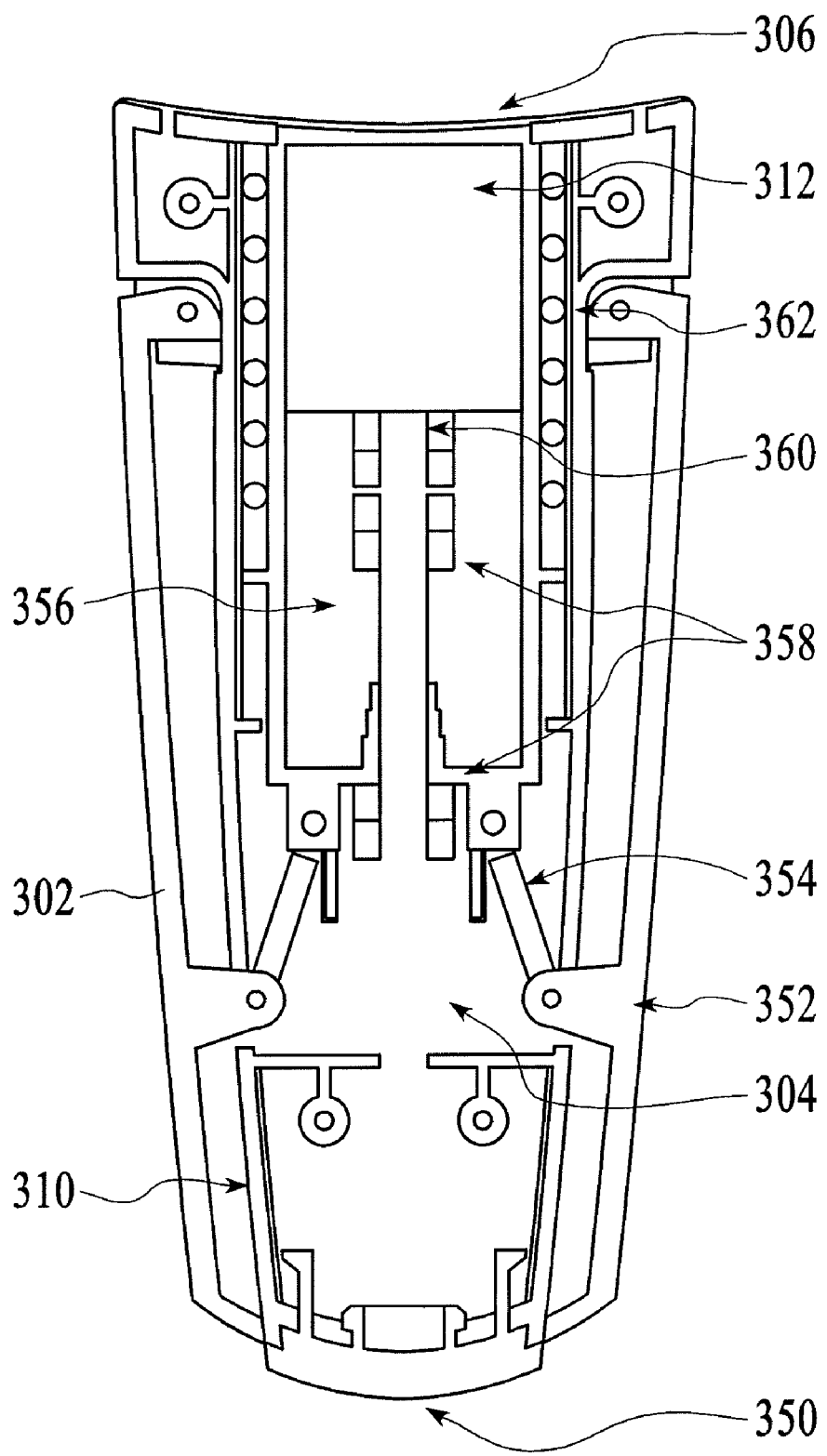
FIG. 8(a) shows a side, cross-sectional view of a magnetic device with a retractable second magnetic structure. The magnetic device shown in FIG. 8(a) is at full magnetic power.

FIG. 8(a) shows a side, cross-sectional view of a magnetic device 300 according to an embodiment of the invention. A front portion of the device 300 includes a silicone pad 306 for skin protection. A second magnetic structure 312 is shown as being adjacent to the silicone pad 306, and is in a "full magnetic power" position. A spring 362 biases the second magnetic structure 312 rearward, in the absence of pressure on the handles 302. Linking structures 354 pivotably link the handles 302 and a cylindrical structure 356 holding the second magnetic structure 312, so that the inward depression of the handles 302 cause the second magnetic structure 312 to move toward the front of the magnetic device 300. A cap 350 is provided at the rear of the magnetic device 300 in order to hide the internal components (e.g., the power adjust mechanism) of the magnetic device. The cap 350 may be attached to a housing 310, which houses components such as the cylindrical structure 356, the second magnetic structure 312, the spring 362, and the linking structure 354.

A threaded screw structure 304 and a number of stops 358 may also be provided in the magnetic device 300. These components may be used to adjust the position of the second magnetic structure 312 within the magnetic device 300 so that the magnetic power of the magnetic device 300 can be correspondingly adjusted by a patient.

As shown in FIG. 8(a), the second magnetic structure 312 can be positioned anywhere within the magnetic device 300 so that the magnetic power of the magnetic device 300 can be adjusted to a desired level.

Figure 8B:
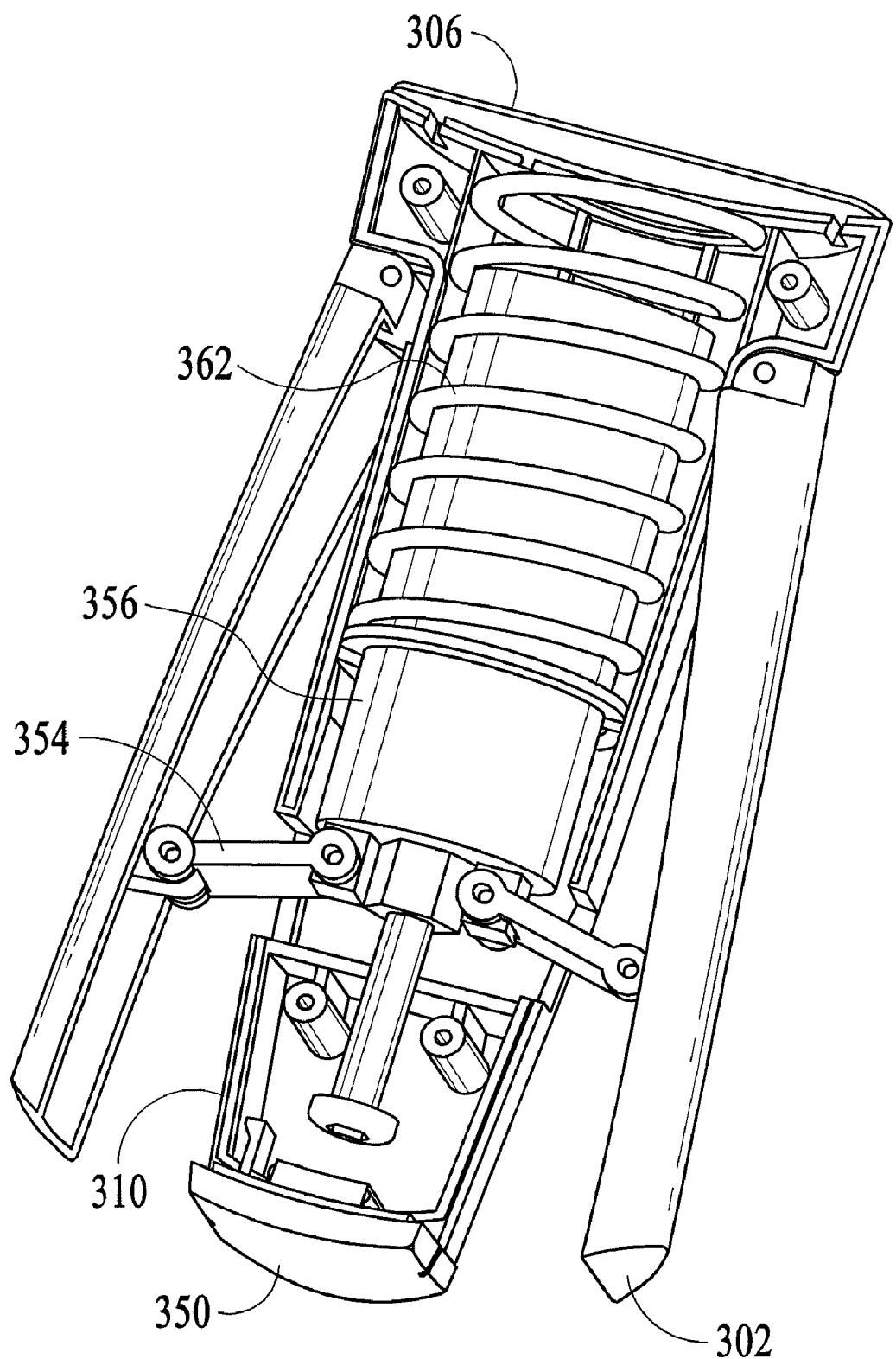
FIG. 8(b) shows a side, cross-sectional view of a magnetic device of the type shown in FIG. 8(a). The magnetic device is not at full power and a second magnetic structure that is inside of a cylindrical structure is in a partially retracted position.

FIG. 8(b) shows a side, cross-sectional view of a magnetic device of the type shown in FIG. 8(b). In FIG. 8(b), like numerals designate like elements as in FIG. 8(a). The magnetic device is not at full power and a second magnetic structure that is inside of a cylindrical structure is in a partially retracted position. The handles 302 project outward when the second magnetic structure is in a retracted position.

As described above, preferred embodiments of the invention use magnetic structures and magnetic devices to open a patient's passageway. However, in other embodiments, magnetic structures and devices are not needed. For example, in one embodiment of the invention, a structure such as a suture can placed around the cricoid cartilage in individuals with oropharyngeal dysphagia. When the suture is pulled forward, the cricopharyngeous (CP) muscle pulls forward and opens up the cervical esophagus. A handle or other structure may be coupled to the suture to help the patient pull the suture forward. Patients who were previously unable to swallow are able to eat with this simple suture in place. The suture goes through the skin and stays in place. The suture could be susceptible to infection so appropriate measures can be taken to reduce the risk of infection. For example, the suture may be coated with a biocompatible material which would reduce the risk of infection.

Figure 9:
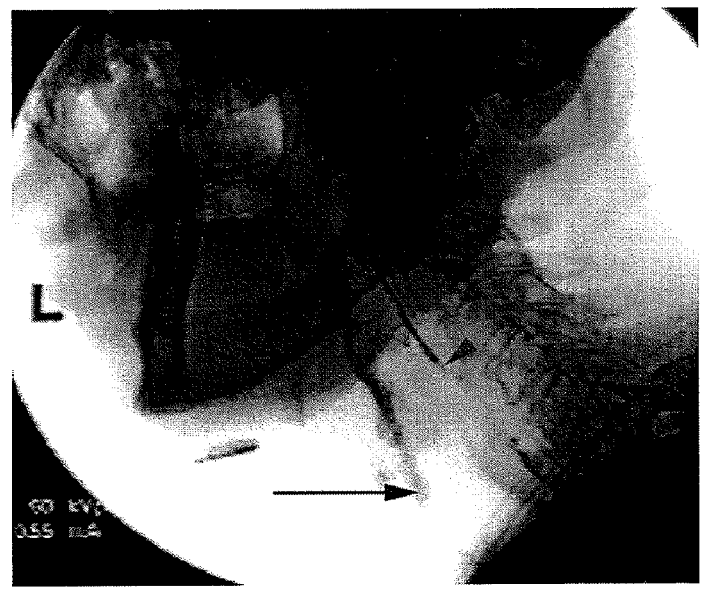
FIGS. 9-10 show two images from a fluoroscopic swallow evaluation before and after pulling on a cricoid structure.
Figure 10:
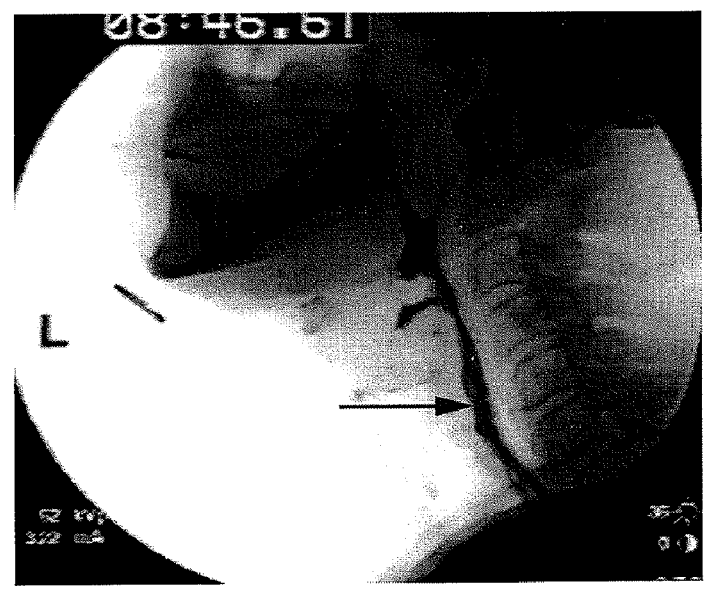

FIGS. 9-10 show two images from a fluoroscopic swallow evaluation before and after pulling on a cricoid suture. In FIG. 9, the patient aspirated without traction on the suture and was not able to pass any food into his esophagus. The upper esophageal sphincter (UES) does not open causing the barium column to impede (arrowhead). Because the UES does not open, the food has nowhere to go but into the trachea, resulting in aspiration. Barium can be seen crossing the vocal folds into the proximal trachea (arrow).

Referring to FIG. 10, with traction on the suture, the patient was able to pass food safely into his esophagus without any aspiration. In FIG. 10, the same patient as in FIG. 9 is placing anterior traction on a suture placed around the cricoid cartilage during the swallow. The UES is now open and the barium passes easily into the esophagus without any aspiration (arrow). The embodiments of the invention that use the magnetic structures can provide more anterior traction than the simple suture and the improvement in swallowing should be even more dramatic.

Although the use of a cricoid suture is acceptable, as noted above, preferred embodiments of the invention use an implanted magnetic structure that is secured to the cricoid cartilage. Because the magnetic structure in the preferred invention embodiments is secured directly to the cricoid, it will provide better anterior traction to open the upper sphincter of the esophagus than a lone suture and the improvement in swallowing should be even greater than using a long suture as a means for opening the esophagus. Also, because the magnetic structure is implanted under the skin, it will not serve as a source for infection. Thus, the embodiments of the invention that use magnetic devices and magnetic structures to open a patient's passageway have a number of advantages over embodiments using sutures as a traction mechanism.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed.

Moreover, one or more features of one or more embodiments of the invention may be combined with one or more features of other embodiments of the invention without departing from the scope of the invention.

All patents, patent applications, publications, and descriptions mentioned above are herein incorporated by reference in their entirety for all purposes. None is admitted to be prior art.

What is claimed is:

1. A method for opening a passageway in a patient, the method comprising:
   placing a structure in the patient, wherein the structure is attached to the cricoid cartilage in the patient's neck; and
   pulling the structure away from the patient to open the passageway, wherein the passageway is an esophagus in the patient, and wherein pulling the structure allows the patient to control the opening of the upper sphincter of the esophagus.

2. A method for opening a passageway in a patient, the method comprising:
   placing a structure in the patient, wherein the structure is attached to the cricoid cartilage in the patient's neck; and
   pulling the structure away from the patient to open the passageway, wherein the passageway is an esophagus in the patient, and wherein pulling the structure allows the patient to control the opening of the upper sphincter of the esophagus,
   wherein the structure is metallic.

* * * * *